(12) United States Patent
Maile et al.

(10) Patent No.: US 8,929,041 B2
(45) Date of Patent: Jan. 6, 2015

(54) ELECTROSTATIC DISCHARGE PROTECTION CIRCUIT

(71) Applicant: Cardiac Pacemakers, Inc., St. Paul, MN (US)

(72) Inventors: Keith R. Maile, New Brighton, MN (US); William J. Linder, Golden Valley, MN (US); Lance E. Juffer, Lino Lakes, MN (US); Nicholas J. Stessman, Minneapolis, MN (US); Ron A. Balczewski, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 156 days.

(21) Appl. No.: 13/755,948

(22) Filed: Jan. 31, 2013

(65) Prior Publication Data

US 2013/0208383 A1    Aug. 15, 2013

Related U.S. Application Data

(60) Provisional application No. 61/597,461, filed on Feb. 10, 2012.

(51) Int. Cl.
*H02H 9/00* (2006.01)
*H02H 9/04* (2006.01)
*A61N 1/37* (2006.01)

(52) U.S. Cl.
CPC ............. *H02H 9/041* (2013.01); *A61N 1/3718* (2013.01); *H02H 9/46* (2013.01)
USPC .......................................................... 361/56

(58) Field of Classification Search
USPC .......................................................... 361/56
See application file for complete search history.

(56) References Cited

U.S. PATENT DOCUMENTS 5,264,723 A    11/1993 Strauss
5,514,995 A    5/1996 Hennig
(Continued)

FOREIGN PATENT DOCUMENTS

WO    WO-03081742 A1    10/2003

OTHER PUBLICATIONS

Chiu, Po-Yen, et al., "Design of Low-Leakage Power-Rail ESD Clamp Circuit with MOM Capacitor and STSCR in a 65-nm CMOS Process", 2011 IEEE International Conference on IC Design & Technology (ICICDT),, (May 2-4, 2011), 4 pgs.

(Continued)

*Primary Examiner* — Stephen W Jackson
(74) *Attorney, Agent, or Firm* — Schwegman Lundberg & Woessner, P.A.

(57) ABSTRACT

An integrated circuit for an implantable medical device can include a substrate, a first capacitor, and an electrostatic discharge (ESD) protection circuit. The first capacitor can include an electrically conductive lower polysilicon terminal and an electrically conductive upper polysilicon terminal that can be separated from the lower polysilicon terminal by a first capacitor dielectric material. The ESD protection circuit can include an ESD shunt transistor and a second capacitor. The ESD shunt transistor can be configured to be normally off, but can be configured to turn on and conduct between first and second power supply rails in response to an ESD event exceeding a specified ESD event threshold value. The second capacitor can includes a first substrate terminal and an electrically conductive second polysilicon terminal that can be separated from the first substrate terminal by a second capacitor dielectric material.

20 Claims, 8 Drawing Sheets

(56) References Cited

U.S. PATENT DOCUMENTS

| | | | |
|---|---|---|---|
| 5,670,814 | A * | 9/1997 | Wu et al. .................. 257/360 |
| 6,479,872 | B1 * | 11/2002 | Cheng et al. .............. 257/360 |
| 6,724,603 | B2 | 4/2004 | Miller et al. |
| 7,106,568 | B2 * | 9/2006 | Chen ........................ 361/91.1 |
| 7,755,871 | B2 | 7/2010 | Ker et al. |
| 7,911,748 | B1 | 3/2011 | Chu et al. |
| 2004/0027745 | A1 | 2/2004 | Kunz et al. |
| 2005/0231878 | A1 | 10/2005 | Krasin |
| 2009/0059451 | A1 | 3/2009 | Shi et al. |

OTHER PUBLICATIONS

Chiu, Po-Yen, et al., "Impact of Gate Leakage Current on Power-Rail ESD Clamp Circuit in Nanoscale CMOS Technology", Proc. of 2009 Electronic Technology Symposium, Kaohsiung, Taiwan, (Jun. 19, 2009), 4 pgs.

Chiu, Po-Yen, et al., "Ultra-Low-Leakage Power-Rail ESD Clamp Circuit in Nanoscale Low-Voltage CMOS Process", Reliability Physics Symposium, 2009 IEEE International, (Apr. 26-30, 2009), 4 pgs.

Dunn, J S, et al., "Foundation of rf CMOS and SiGe BiCMOS technologies", IBM J. Res. & Dev. vol. 47 No. 2/3 Mar./May 2003, (2003), 101-138.

Ker, Ming-Dou, "Area-Efficient VDD-to-VSS ESD Clamp Circuit by Using Substrate-Triggering Field-Oxide Device (STFOD) for Whole-Chip ESD Protection", VLSI Technology, Systems, and Applications, 1997. Proceedings of Technical Papers. 1997 International Symposium on VLSI Design Department, Computer & Communication Research Laboratories (CCL) Industrial Technology Research Institute (ITN), Hsinchu, Taiw, (Jun. 3-5, 1997), 69-73.

Ker, Ming-Dou, et al., "Design on the Turn-On Efficient Power-Rail ESD Clamp Circuit With Stacked Polysilicon Diodes", ISCAS 2001. The 2001 IEEE International Symposium on Circuits and Systems, 2001. Integrated Circuits & Systems Laboratory, Institute of Electronics National Chiao Tung University, Hsinchu, Taiwan, (May 6, 2001-May 9, 2001), IV-758-IV-761.

Ker, Ming-Dou, et al., "Whole-Chip ESD Protection for CMOS VLSI/ULSI With Multiple Power Pins", IRW Final Report, (1994), 124-128.

Worley, E R, et al., "Sub-Micron Chip ESD Protection Schemes Which Avoid Avalanching Junctions", EOS/ESD Symposium 95-13 Rockwell Telecommunications 431 1 Jamboree Rd, Newport Beach, CA 92658-8902, (Sep. 12, 1995), 1.2.1-1.2.8.

* cited by examiner

ELECTROSTATIC DISCHARGE PROTECTION CIRCUIT

CLAIM OF PRIORITY

This application claims the benefit of priority under 35 U.S.C. §119(e) of Maile et al., U.S. Provisional Patent Application Ser. No. 61/597,461, entitled "ELECTROSTATIC DISCHARGE PROTECTION CIRCUIT", filed on Feb. 10, 2012, which is herein incorporated by reference in its entirety.

BACKGROUND

Implantable medical devices (IMD) can include, among other things, cardiac rhythm management (CRM) devices such as pacemakers, cardioverters, defibrillators, cardiac resynchronization therapy (CRT) devices, or neuro-stimulation systems such as spinal cord stimulation (SCS) systems, or combination devices that can provide more than one of these or other therapy modalities to a subject. An IMD can include or use an Integrated Circuit (IC) that can provide one or multiple power supplies such as to treat one or more living organs, for example, by pacing the heart. Since the IC generally controls the operation of the IMD, it can be important to protect the IC from damage caused by excess voltage supplied to the IC.

Excess voltage resulting in damage to the IC can be caused by electrostatic discharge (ESD). Electrostatic discharge (ESD) is the sudden and momentary electric current that flows between the plates of a capacitor at different electrical potentials. ESD can lead to momentary unwanted currents that may cause damage to electronic equipment. An ESD event can be characterized by its amplitude and spectral content, and can include a characteristic ESD event threshold. The ESD event threshold can be characterized as a characteristic voltage applied using one of the following ESD models: human body model (HBM), machine model (MM), or charged device model (CDM).

In order to avoid the electrostatic discharge, an ESD clamp can be used. The ESD clamp is a circuit that can be configured to divert a potentially damaging charge away from the sensitive circuitry and protect the system from damage. An IC with multiple power supplies can use one or more protection circuits, such as between adjacent bond pads, to inhibit or prevent the damage caused to the IC by an excess voltage supplied to the IC. The ESD clamps can have a high-pass filter characteristic so that they respond to ESD events (which have high spectral content, or rapid change in voltage) without responding to non-ESD voltage excursions, such as can occur during or after the device is powered up. ESD clamps can have high pass filter characteristic time constant (T), e.g., ranging from 0.1 microsecond to 1 microsecond.

OVERVIEW

One approach to ESD protection can be to use a polysilicon-oxide-polysilicon capacitor (poly-poly capacitor) in the ESD protection circuit of an IMD. The poly-poly capacitor allows respective plates of the capacitor to be respectively driven over a range of voltages or potentials. However, these ESD protection circuits may be stressed during constant bias conditions. The poly-poly capacitor may degrade if it is subjected to a constantly biased electric field (e.g., around 12 volts (V), which may be susceptible to a Time Dependent Dielectric Breakdown (TDDB) phenomenon.) The TDDB is a mechanism in which a dielectric layer of the capacitor breaks down as a result of long-time application of relatively low electric field. The TDDB is an indicator of the dielectric's ability to withstand constantly biased electric field. The breakdown is caused by formation of a conducting path through the dielectric layer to substrate due to electron tunneling current ("leakage current"). The electron tunneling current is generated due to long time application of relatively low electric field and some imperfections in the dielectric in the form of crystal boundaries. Breakdown of the dielectric layer of the poly-poly capacitor, in the ESD protection circuit of an IMD, may damage the poly-poly capacitor and may cause a high current condition that can deplete a battery of the IMD. Depletion of the battery may hinder the functioning of IMDs.

In an example, the present subject matter relates to an integrated circuit (IC) of an IMD. The IC can include a substrate, a first capacitor, and an ESD protection circuit. The first capacitor can include an electrically conductive lower polysilicon terminal and an electrically conductive upper polysilicon terminal that can be separated from the lower polysilicon terminal by a first capacitor dielectric material. The ESD protection circuit can include an ESD shunt transistor and a second capacitor. The ESD shunt transistor can be configured to remain off normally, but it can also be configured to turn on and conduct between the first and second power supply rails in response to an ESD event with voltage or energy exceeding a specified threshold value. The second capacitor can include a first substrate terminal and an electrically conductive second polysilicon terminal that can be separated from the first substrate terminal by a second capacitor dielectric material.

This overview is intended to provide an overview of the subject matter of the present patent application. It is not intended to provide an exclusive or exhaustive explanation of the present subject matter. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of an example, but not by way of limitation, various embodiments discussed in the present document.

DETAILED DESCRIPTION

Figure 1:
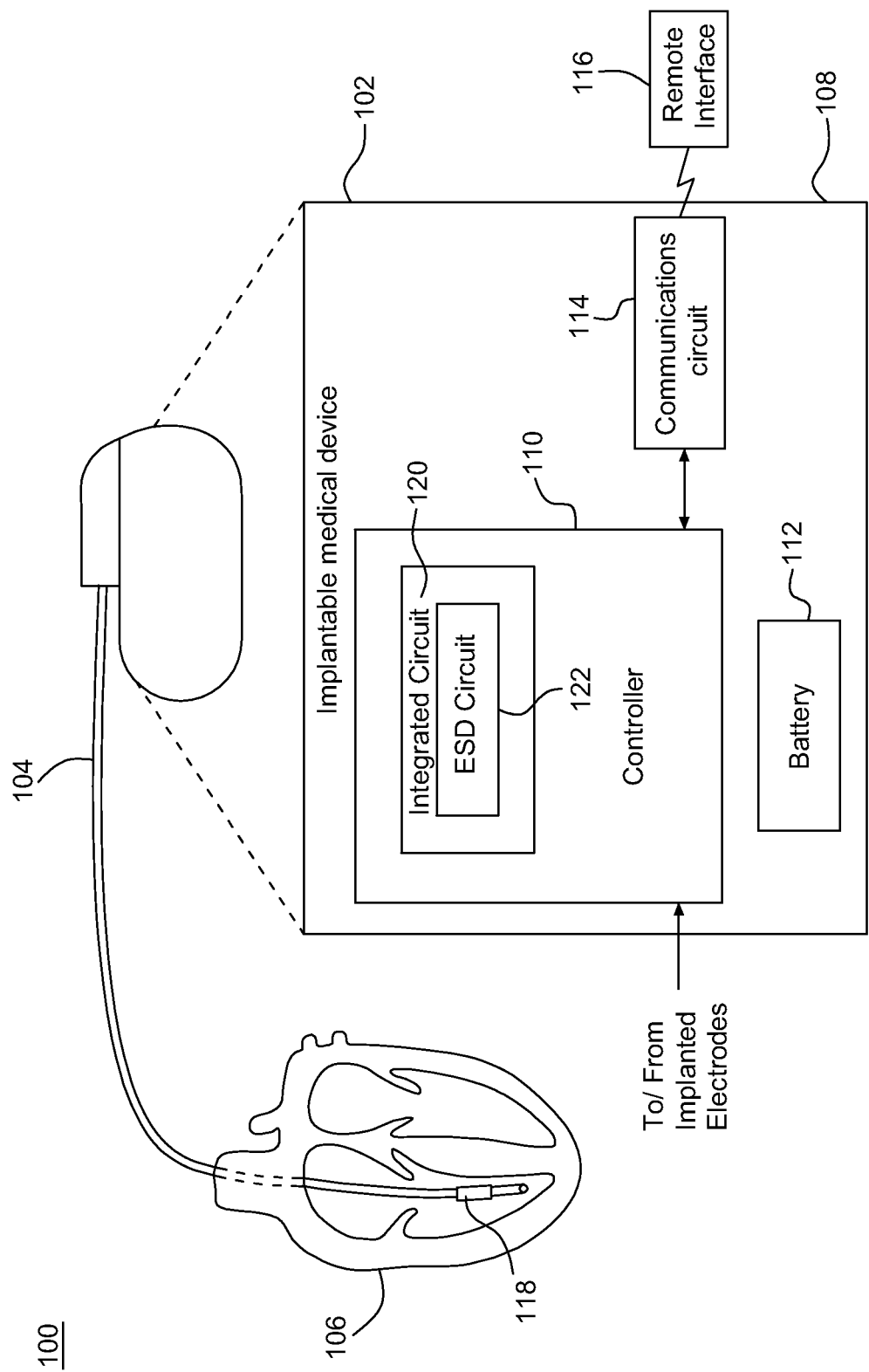
FIG. 1 is a block diagram illustrating generally, by way of an example, but not by way of limitation, portions of an IMD and portions of an environment in which it is used.

FIG. 1 is a block diagram illustrating generally, by way of an example, but not by way of limitation, portions of an Implantable Medical Device (IMD) and portions of an environment in which it is used. In an example, a system 100 can include, among other things, an IMD 102 and a lead wire 104. The lead wire 104 can be coupled to the IMD 102 and can act as an interface between the IMD 102 and a portion of a living organism or other subject, such as heart 106. The IMD 102 can include a housing 108. The housing 108 can include, among other things, a controller 110, a battery 112, and a communication circuit 114. The communication circuit 114 can be adapted for wireless communication with a remote interface 116 as shown in FIG. 1. The controller 110 can be coupled, such as via a sensing circuit or an electrostimulation or other circuit, to one or more electrodes 118 through the lead wire 104. In an example, one or more of the electrodes 118 can be attached to the surface of a myocardium of the heart 106. The electrodes 118 can deliver pacing stimulations or other electrical energy to the heart 106. The controller 110, among other things, can include an integrated circuit 120. The integrated circuit 120 can include an electrostatic discharge (ESD) protection circuit 122. Illustrative examples of the IMD 102 can include, among other things, a bradycardia or antitachycardia pacemaker, a cardioverter, a defibrillator, a combination pacemaker/defibrillator, a cardiac resynchronization therapy device, a drug delivery device, or other implantable device.

Figure 2:
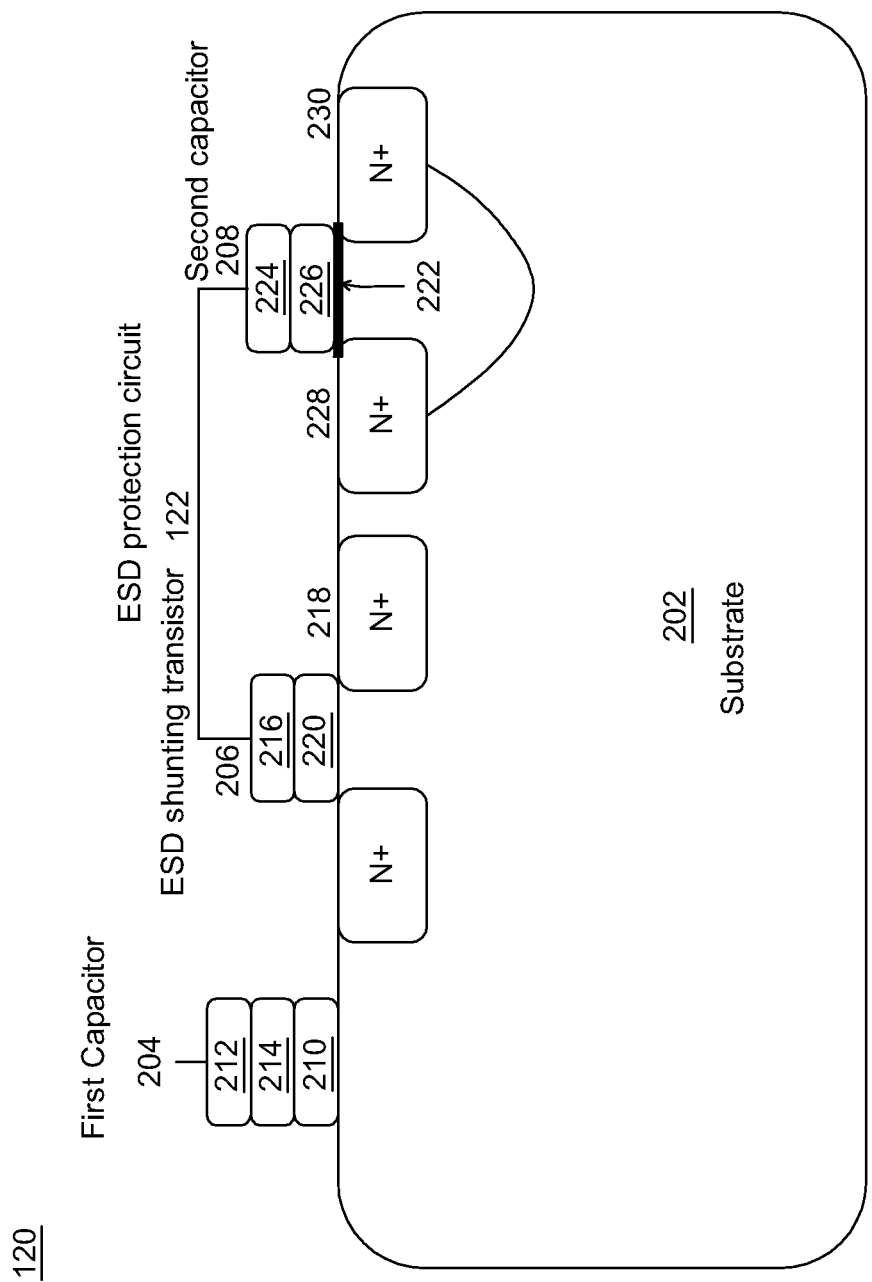
FIG. 2 illustrates generally, by way of an example, but not by way of limitation, an integrated circuit of the IMD.

FIG. 2 illustrates generally, by way of an example, but not by way of limitation, the integrated circuit 120 of the IMD 102. The integrated circuit 120, among other things, can include a substrate 202, a first capacitor 204, and the ESD protection circuit 122. The ESD protection circuit 122 can include, among other things, an ESD shunt transistor 206 and a second capacitor 208. In an example, a size of the second capacitor 208 can be comparable to a size of the first capacitor 204. The size of the capacitor characterizes the area of the plates and the distance between the plates of the capacitor, which determine the charge that can be stored by the capacitor. In an example, the second capacitor 208 can be of 100 Pico Farad (pF), charged to 2000V using a 1500 Ohm (Ω) resistor in an ESD event. In an example, the first capacitor 204 can store similar amounts of charge as compared to the charge stored in the second capacitor 208 when subjected to the same voltage. In an example, the substrate 202 can include an n-type semiconductor substrate. In an example, the substrate 202 can include a p-type semiconductor substrate.

The first capacitor 204 can be located directly or indirectly upon the substrate 202. The first capacitor 204 can include an electrically conductive lower polysilicon terminal 210 and an electrically conductive upper polysilicon terminal 212. The upper polysilicon terminal 212 can be separated from the lower polysilicon terminal 210 by a first capacitor dielectric material 214. Fabrication of the first capacitor 204 can occur in three distinct phases. The lower polysilicon terminal 210 can be deposited in the first phase; the first capacitor dielectric material 214 can be deposited in the second phase; and the upper polysilicon terminal 212 can be deposited in the third phase. The first capacitor dielectric material 214 can include a material other than a native or dry-grown oxide. The first capacitor dielectric material 214 can include a deposited oxide. In an example, the first capacitor dielectric material 214 can include a spun-on oxide. In an example, the first capacitor dielectric material 214 can include a sputtered oxide. In an example, the first capacitor dielectric material 214 can include a chemically deposited oxide. A chemical vapor deposition (CVD) process can be used to deposit the first capacitor dielectric material 214. In an example, the first capacitor dielectric material 214 can include any other dielectric material and other processes may be used to deposit it.

The ESD shunt transistor 206 can include a field-effect transistor. The ESD shunt transistor 206 can include a gate 216, a first source/drain 218, and a second source/drain 220. The second capacitor 208 can be coupled between a first source/drain 218 and the gate 216 of the ESD shunt transistor 206. The ESD shunt transistor 206 can be configured to remain off normally. But the ESD shunt transistor 206 can be configured such that, in response to an ESD event, such as with an ESD event voltage that exceeds a specified ESD event threshold value, the ESD shunt transistor 206 can turn on and conduct current between the first and second power supply rails.

The second capacitor 208 can be located directly or indirectly upon the substrate 202. The second capacitor 208 can include a first substrate terminal 222 and an electrically conductive second polysilicon terminal 224 that can be separated from the first substrate terminal 222 by a second capacitor dielectric material 226. The first substrate terminal 222 can be located on a first substrate region. In an example, a gate oxide can be used as the second capacitor dielectric material 226 of the second capacitor 208. In an example, another dielectric can be used as the second capacitor dielectric material 226 of the second capacitor 208. In an example, the first substrate region can be located in the well region of the substrate 202. In an example, the first substrate region can be located in an epitaxial region of the substrate 202.

The ESD shunt transistor 206 can include the gate 216, a first source/drain 218, and a second source/drain 220. The gate 216 of the ESD shunt transistor 206 can serve as the second poly-silicon terminal 224 of the second capacitor 208. The first source/drain region 228 of the ESD shunt transistor 206 can be electrically shorted to the second source/drain region 230 of the ESD shunt transistor 206 to form the first substrate terminal 222 of the second capacitor 208. The ESD shunt transistor 206 can have a length that can be substantially equivalent to a specified minimum transistor length in a fabrication process used to fabricate the integrated circuit 120. The second capacitor 208 can include a depletion-mode or enhancement mode capacitor that can be sized or otherwise configured to provide a specified capacitance value to contribute to the specified ESD event threshold value.

The second capacitor dielectric material 226 can include a native or grown oxide, such as on a monocrystalline region of the substrate 202. The second capacitor dielectric material 226 can be grown on the substrate 202 using a dry growth process, with the resulting oxide sometimes referred to as a "thermally grown oxide" or "native oxide." The dry growth process can make the second capacitor dielectric material 226 stronger than the first capacitor dielectric material 214, which can include a material other than native or dry grown oxide, such as a wet-grown oxide. A dry growth process is a relatively slower process than wet-growth, but produces less imperfections in the resulting oxide. A wet growth process is faster, and need not require a monocrystalline structure of an underlying substrate. Wet grown oxide is more prone to voids, broken silicon or oxygen bonds, or contamination. Such dielectric imperfections can result in small leakage current flowing through the dielectric material due to the powerful electric fields occurring when a voltage is applied to the capacitor, which can degrade reliability.

The first capacitor dielectric material 214 of the first capacitor 204 can be wet grown over a polycrystalline region. Hence, the first capacitor dielectric material 214 can include a plurality of non-planar crystal boundaries, which can propagate defects into the dielectric during the wet growth. In contrast, the second capacitor dielectric material 226 of the second capacitor 208 can be grown over a monocrystalline region of a lightly doped substrate 202, thereby propagating fewer defects into the dielectric. Therefore, the second capacitor dielectric material 226 of the second capacitor 208 can have a different dielectric constant and less leakage current than the first capacitor dielectric material 214 of the first capacitor. These differences can delay a time-dependent dielectric breakdown (TDDB) phenomenon of the second capacitor dielectric material 226 beyond that of the first capacitor dielectric material 214 of the first capacitor 204. Thus, the second capacitor dielectric material 226 of the second capacitor 208 can withstand the dielectric breakdown for a longer period as compared to the first capacitor dielectric material 214 of the first capacitor 204.

A thickness of the second capacitor dielectric material 226 separating the first substrate terminal 222 from the second polysilicon terminal 224 of the second capacitor 208 can be less than a thickness of the first capacitor dielectric material 214 separating the lower and upper polysilicon terminals of the first capacitor 204. In an example, a thickness of the second capacitor dielectric material 226 of the second capacitor 208 can be around 290 Angstroms (Å) and the thickness of the first capacitor dielectric material capacitor of the first capacitor 204 can be around 390 Å.

Generally, a thicker-dielectric capacitor would be used in an ESC protection circuit application—because of the increased ability to withstand a high voltage provided by the thicker capacitor dielectric. However, the present inventors have recognized that although the thickness of the first capacitor dielectric material 214 can be more than the thickness of the second capacitor dielectric material, over a longer period of time, the first capacitor 204 may not be more reliable than the second capacitor 208 in the ESD protection circuit 122, due to the reduced TDDB susceptibility provided by the dry growth process of the second capacitor dielectric material, as explained herein.

In an example, the second capacitor 208 has a limited conductivity because the first substrate terminal 222 of the second capacitor 208 is attached to the substrate 202. A capacitance of the second capacitor 208 can be dependent on voltage applied across its two terminals as a result of the enhancement and the depletion regions of the first substrate terminal 222. Hence, the capacitance of the second capacitor 208 can be non-linear.

In an example, the first capacitor 204 can be configured to allow terminal plates of the first capacitor 204 to function at any driven voltage potential, thereby offering flexibility. Further, the second capacitor 208 may have a larger capacitance value than the first capacitor 204.

A capacitance value of the first capacitor 204 and a trigger voltage of the ESD protection circuit 122 can be adjusted, such as by adjusting a layout area of the first capacitor 204. Therefore, the ESD protection circuit 122 may have improved ESD performance by using the first capacitor 204 than by using the second capacitor 208 as the second capacitor may be coupled with the ESD shunt transistor 206. The adjustment of the capacitance value of the first capacitor 204 can involve only one mask adjustment and can be easy to implement. In an example, using the first capacitor 204 in the ESD protection circuit 122 need not increase the circuit area of the ESD protection circuit 122 because the first capacitor 204 can be integrated with the ESD shunt transistor 206 on the same substrate 202.

Although the first capacitor 204 would appear to provide certain advantages over the second capacitor 208 in the ESD protection circuit 122, the second capacitor 208 can be more reliable than the first capacitor 204 in the ESD protection circuit 122, due to its reduced TDDB susceptibility, as explained herein. Since reliability can be an important criterion for choosing a capacitor for the ESD protection circuit in the integrated circuit for the IMD, the second capacitor 208 can be used in the ESD protection circuit 122 even when the first capacitor 204 is also available on the same integrated circuit 120.

Figure 3:
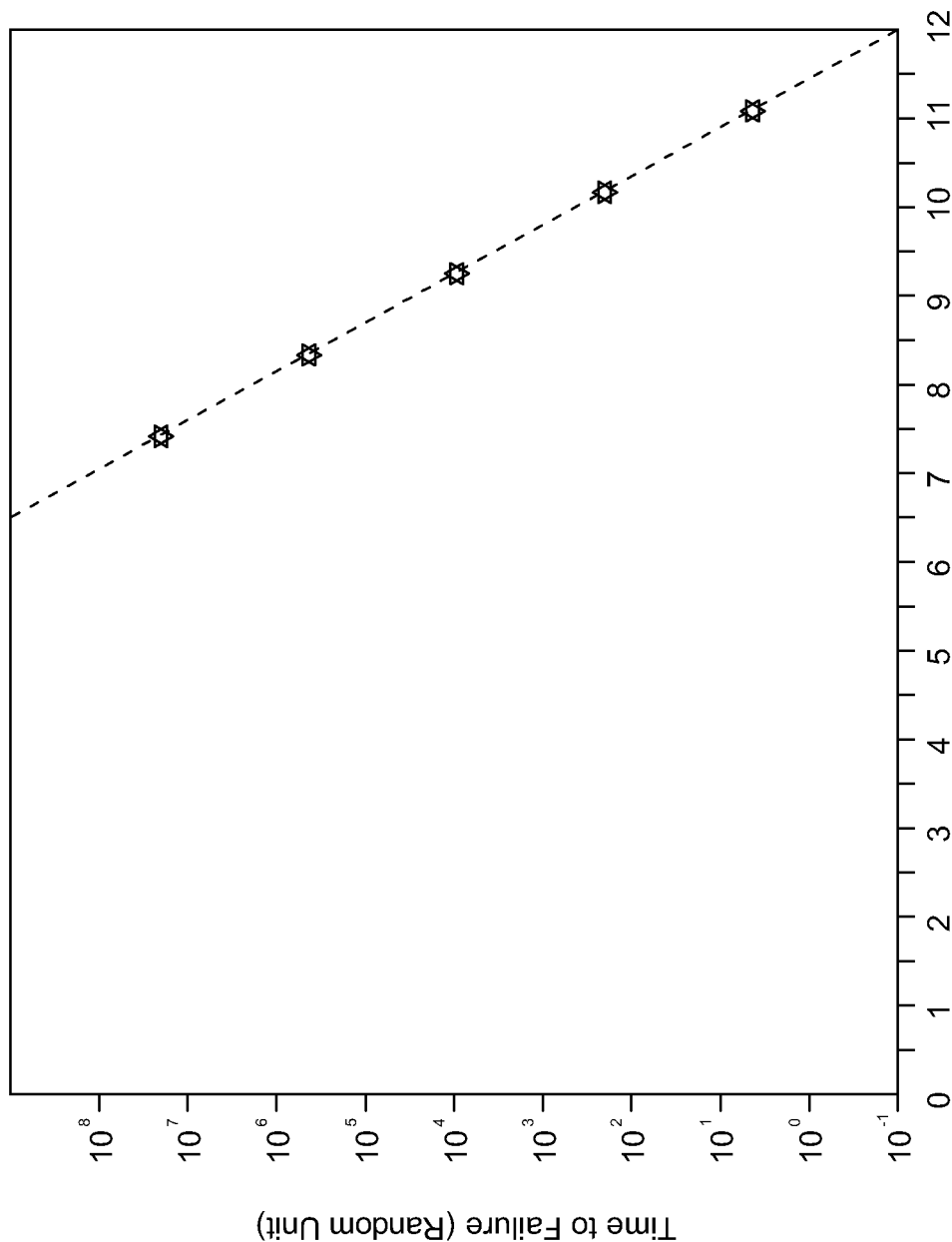
FIG. 3 is a graph that illustrates generally a relationship between electric field and time-to-failure of a dielectric material.

FIG. 3 is a graph that illustrates generally a relationship between electric field and time-to-failure of a dielectric material. The time-to-failure decreases as the electric field is increased. For a given voltage, the electric field applied on a dielectric material of a capacitor depends upon the thickness of the dielectric material in the capacitor (E=V/t, wherein 'V' represents voltage and 't' represents thickness). The electric field applied is higher in a thin dielectric material than in a thick dielectric material for a given voltage. The thickness of the second capacitor dielectric material 226 of the second capacitor 208 can be less than the thickness of the first capacitor dielectric material 214, separating the lower and upper polysilicon terminals of the first capacitor 204. Hence, the electric field applied on the second capacitor dielectric material 226 can be higher than the electric field applied on the first capacitor dielectric material 214. As per the graph of FIG. 3, the time-to-failure of the dielectric material decreases as the electric field is increased. Hence, a time-to-failure of the second capacitor dielectric material 226 can be higher than a time-to-failure of the first capacitor dielectric material 214 and the second capacitor 208 can be more reliable than the first capacitor 204.

Figure 4:
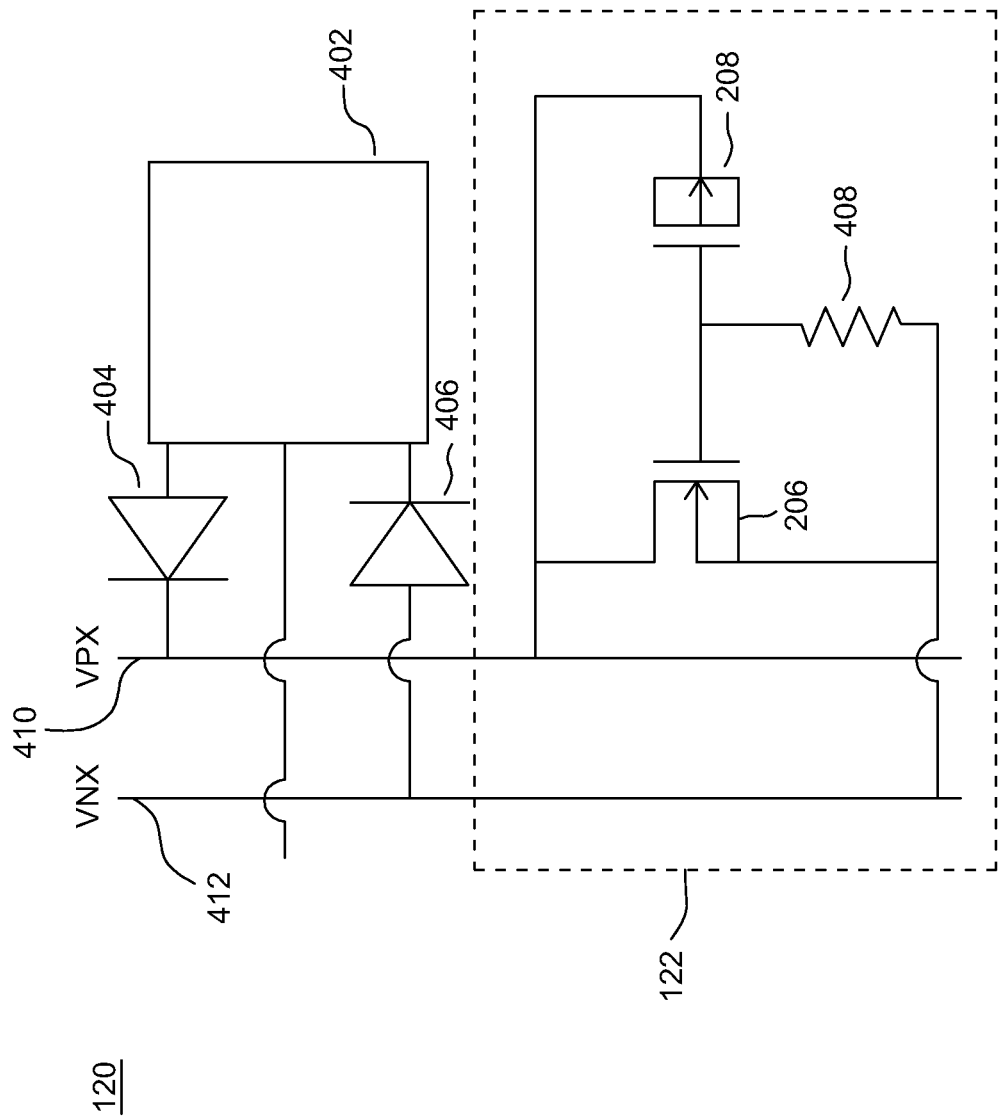
FIG. 4 is a schematic diagram illustrating generally, by way of an example, but not by way of limitation, an integrated circuit of the IMD.

FIG. 4 is a schematic diagram illustrating generally, by way of an example, but not by way of limitation, the integrated circuit 120. As shown in FIG. 4, the integrated circuit 120 can include the ESD protection circuit 122, a bond pad 402, a first diode 404, a second diode 406, and a resistor 408. The integrated circuit 120 can be carried within the housing 108 of the IMD 102.

The integrated circuit 120 can include a plurality of bond pads. The ESD protection circuit 122 can be between the bond pad 402 and an adjacent bond pad. The first diode 404 can be coupled between the bond pad 402 and a first supply rail 410. The first diode 404 can be configured to turn on to clamp a voltage of the bond pad 402 such that it may not exceed a voltage of the first supply rail 410 by more than a turn-on voltage of the first diode 404. The second diode 406 can be coupled between the bond pad 402 and a second supply rail 412. The second diode 406 can be configured to turn on to clamp a voltage of the bond pad 402 such that it may not fall below a voltage of the second supply rail 412 by more than a turn-on voltage of the second diode 406.

As shown in the example of FIG. 4, the ESD protection circuit 122 can include the second capacitor 208, the resistor 408, and the ESD shunt transistor 206. The second capacitor 208 can be coupled to a resistor 408 therefore, a resistance value of the resistor 408, together with the capacitance value of the second capacitor 208, can be specified to contribute to the specified ESD event threshold value. In an example, the second capacitor 208 can be formed of a p-channel Field Effect Transistor (FET). The p-channel field-effect transistor can include a gate, a first source/drain region, and a second source/drain region. The gate of the p-channel FET can be the second polysilicon terminal 224 of the second capacitor 208. The first source/drain region of the p-channel field-effect transistor can be electrically shorted to the second source/drain region of the p-channel field-effect transistor, and can be connected to the first substrate terminal 222 of the second capacitor 208, and a gate dielectric of the p-channel FET can be the second capacitor dielectric material of the second capacitor 208. The second polysilicon terminal 224 of the second capacitor 208 can be connected to the gate of the ESD shunt transistor 206. The first substrate terminal 222 of the second capacitor 208 can be connected to the first supply rail 410. In an example, the ESD shunt transistor 206 can be an n-channel FET. The second source/drain of the ESD shunt transistor 206 can be connected to the second supply rail 412 and the first source/drain of the ESD shunt transistor 206 can be connected to the first supply rail 410.

In an example, the second capacitor 208 can include an n-channel FET. The n-channel field-effect transistor can include a gate, a first source/drain region, and a second source/drain region. The gate of the n-channel FET can be the second polysilicon terminal 224 of the second capacitor 208. The first source/drain region of the n-channel field-effect transistor can be electrically shorted to the second source/drain region of the n-channel field-effect transistor, and connected to the first substrate terminal 222 of the second capacitor 208, and a gate dielectric of the n-channel FET can be the second capacitor dielectric material of the second capacitor 208.

The resistor 408 can be coupled between the gate of the ESD shunt transistor 206 and the second source/drain of the ESD shunt transistor 206. The resistor 408 connects the second capacitor 208 to the ESD shunt transistor 206. Initially, the ESD shunt transistor 206 is turned off. When an ESD event occurs, the ESD shunt transistor 206 turns on and the current starts flowing to the second capacitor 208. The current flow is limited by the resistor 408. The product of the resistance value of the resistor 408 and the capacitance value of the second capacitor 208 form a characteristic time constant, which sets the high-pass filter frequency of the ESD protection circuit 122 so as to be responsive to a high frequency ESD event. In an example, the resistor 408 can be a separate (or independent) component in the ESD protection circuit 122. In an example, the resistor 408 can be provided by a gate of the ESD shunt transistor 206. The gate of the ESD shunt transistor 206 can be extended using an aspect ratio that can provide enough series resistance to implement the ESD event trigger function. The gate of the ESD shunt transistor 206 and the gate of the second capacitor 208 can also be co-integrally formed such as to provide a resistance that is equivalent to a resistance provided by the resistor 408.

Under normal circuit operation conditions, the gate of the ESD shunt transistor 206 can have a low voltage level and hence, the ESD shunt transistor 206 can be turned off. When the first supply rail 410 is exposed to a positive ESD stress with the second supply rail 412 grounded, the resistance value of the resistor 408 (together with the capacitance value of the second capacitor 208), can drive the gate of the ESD shunt transistor 206 to a high enough voltage level to turn the ESD shunt transistor 206 on, to provide a low-impedance path from the first supply rail 410 to the second supply rail 412 to shunt ESD. Providing a low impedance path can ensure that all the ESD current flows through the low impedance path without causing any damage to the IC.

Figure 5:
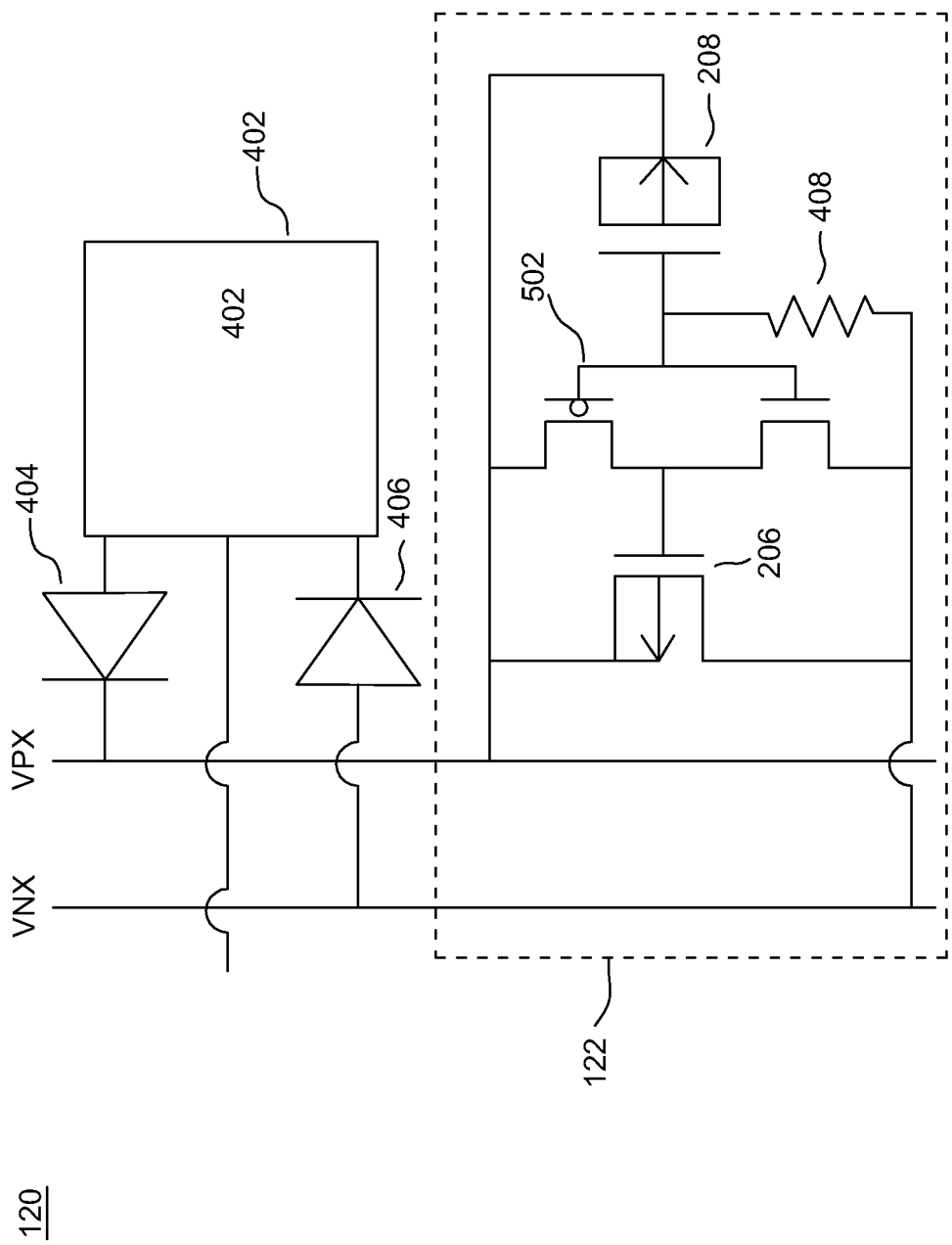
FIG. 5 is a schematic diagram illustrating generally, by way of an example, but not by way of limitation, an integrated circuit of the IMD.

FIG. 5 is a schematic diagram illustrating generally, by way of an example, but not by way of limitation, the integrated circuit 120. As shown in the example of FIG. 5, the integrated circuit 120 can optionally include a buffer circuit 502, the ESD protection circuit 122, the bond pad 402, the first diode 404, and the second diode 406. The buffer circuit 502 can be configured with enough gain to drive control terminal of the ESD shunt transistor 206, along with the second capacitor 208, and the resistor 4080. The buffer circuit can be made inverting or non-inverting to provide the desired signal state at its output.

The buffer circuit 502 can include an input node and an output node. The input node of the buffer circuit 502 can be connected to the second polysilicon terminal 224 of the second capacitor 208. The output node of the buffer circuit 502 can be connected to the gate of the ESD shunt transistor 206. The first substrate terminal 222 of the second capacitor 208 can be connected to the first supply rail 410. In an example, the ESD shunt transistor 206 can be a p-channel field-effect transistor such that the second source/drain of the ESD shunt transistor 206 can be connected to the first supply rail 410 and the first source/drain of the ESD shunt transistor 206 can be connected to the second supply rail 412. The buffer circuit 502 can be configured to enable the ESD shunt transistor 206 to shunt the ESD during an ESD event.

Figure 6:
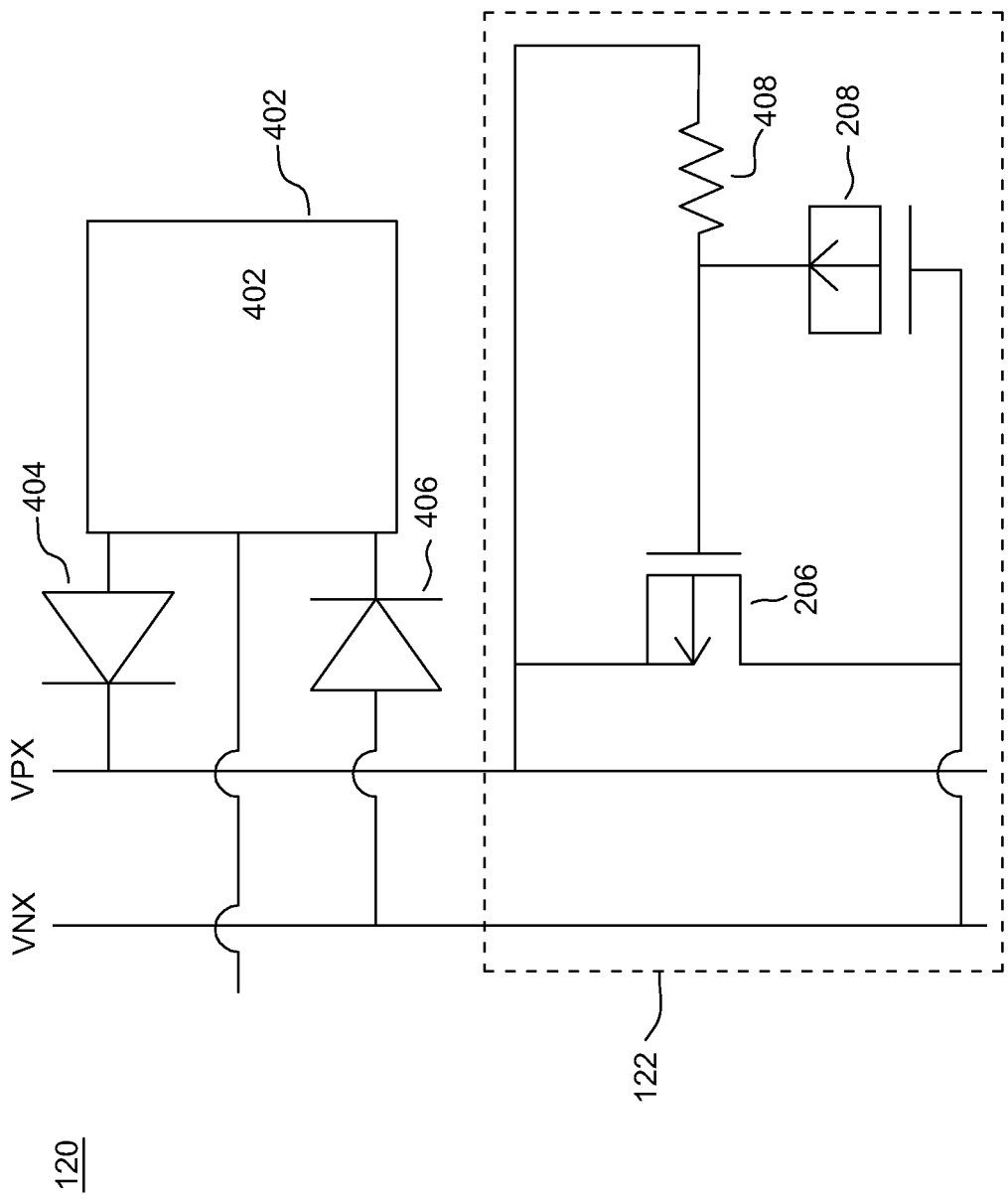
FIG. 6 is a schematic diagram illustrating generally, by way of an example, but not by way of limitation, an integrated circuit of the IMD.

FIG. 6 is a schematic diagram illustrating generally, by way of an example, but not by way of limitation, the integrated circuit 120, such as using a p-channel ESD shunt transistor, rather than the n-channel ESD shunt transistor in the example of FIG. 4. In the example of FIG. 6, the integrated circuit 120 can include the ESD protection circuit 122, the bond pad 402, the first diode 404, and the second diode 406. In an example, the ESD protection circuit 122 can include the second capacitor 208, the resistor 408, and the ESD shunt transistor 206. The second poly-silicon terminal 224 of the second capacitor 208 can be connected to the ESD shunt transistor 206 and the first substrate terminal 222 of the second capacitor 208 can be connected to the second supply rail 412. In an example, the ESD shunt transistor 206 can include a p-channel FET. The second source/drain of the ESD shunt transistor 206 can be connected to the first supply rail 410 and the first source/drain of the ESD shunt transistor 206 can be connected to the second supply rail 412. Thus, in the example of FIG. 6, the second capacitor 208 can be coupled between the gate of the ESD shunt transistor 206 and the first source/drain of the ESD shunt transistor 206. The second capacitor 208 can be connected via the resistor 408 to the second source/drain of the ESD shunt transistor 206.

Figure 7:
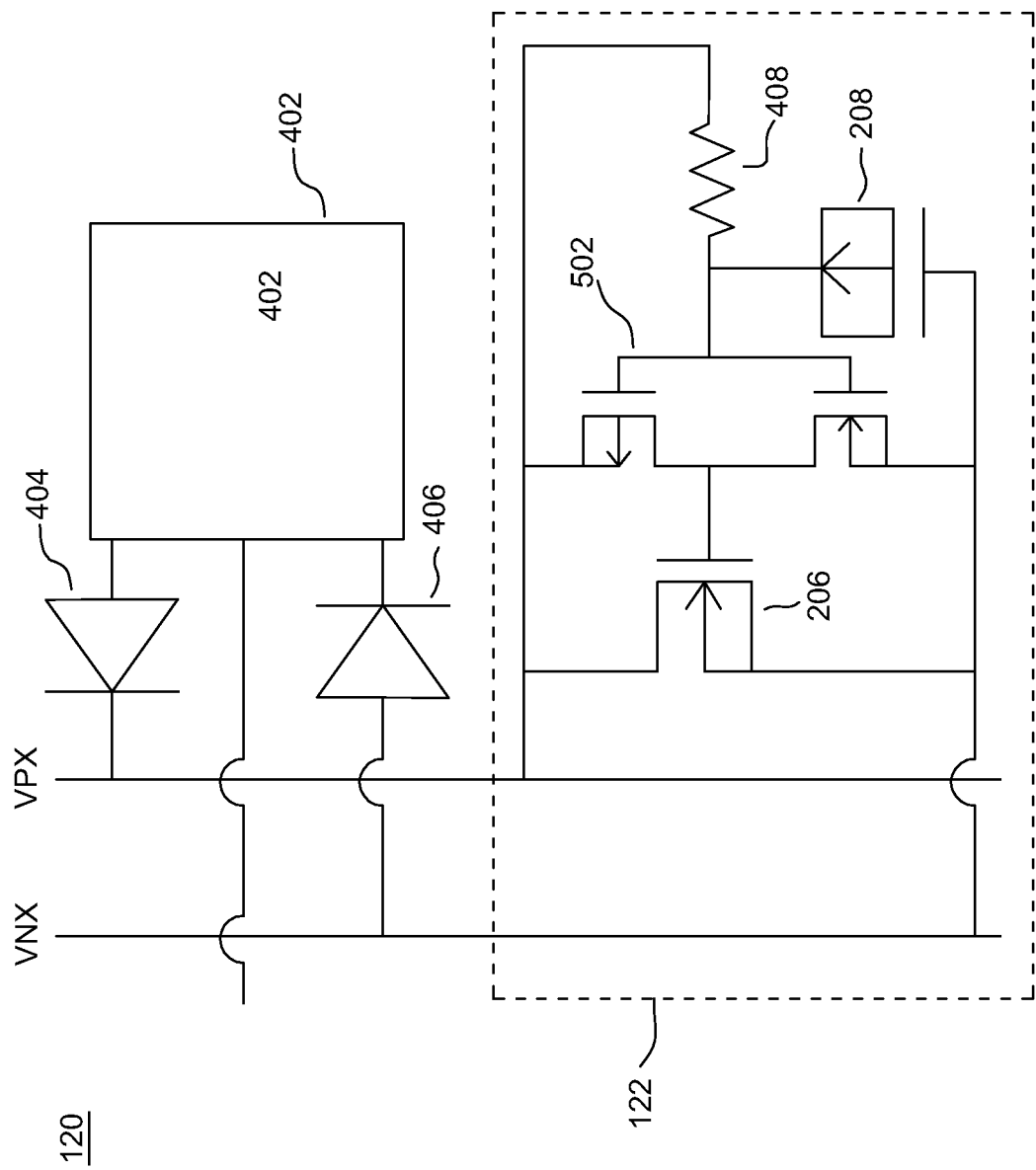
FIG. 7 is a schematic diagram illustrating generally, by way of an example, but not by way of limitation, an integrated circuit of the IMD.

FIG. 7 is a schematic diagram illustrating generally, by way of example, but not by way of limitation, the integrated circuit 120, such as using an n-channel ESD shunt transistor 206 and a buffer. In an example, the integrated circuit 120 can include the ESD protection circuit 122, the bond pad 402, the first diode 404, and the second diode 406. In an example, the ESD protection circuit 122 can include the second capacitor 208, the resistor 408, the ESD shunt transistor 206, and the buffer circuit 502. The buffer circuit 502 can include a non-inverting buffer circuit. The buffer circuit 502 can include an input node and an output node. The input node of the buffer circuit 502 can be connected to the second polysilicon terminal 224 of the second capacitor 208. The output node of the buffer circuit 502 can be connected to the gate of the ESD shunt transistor 206. The first substrate terminal 222 of the second capacitor 208 can be connected to the second supply rail 412. In an example, the ESD shunt transistor 206 can include an n-channel FET. The second source/drain of the ESD shunt transistor 206 can be connected to the second supply rail 412 and the first source/drain of the ESD shunt transistor 206 can be connected to the first supply rail 410. The buffer circuit 502 can be configured to enable the ESD shunt transistor 206 to shunt the ESD during an ESD event.

Figure 8:
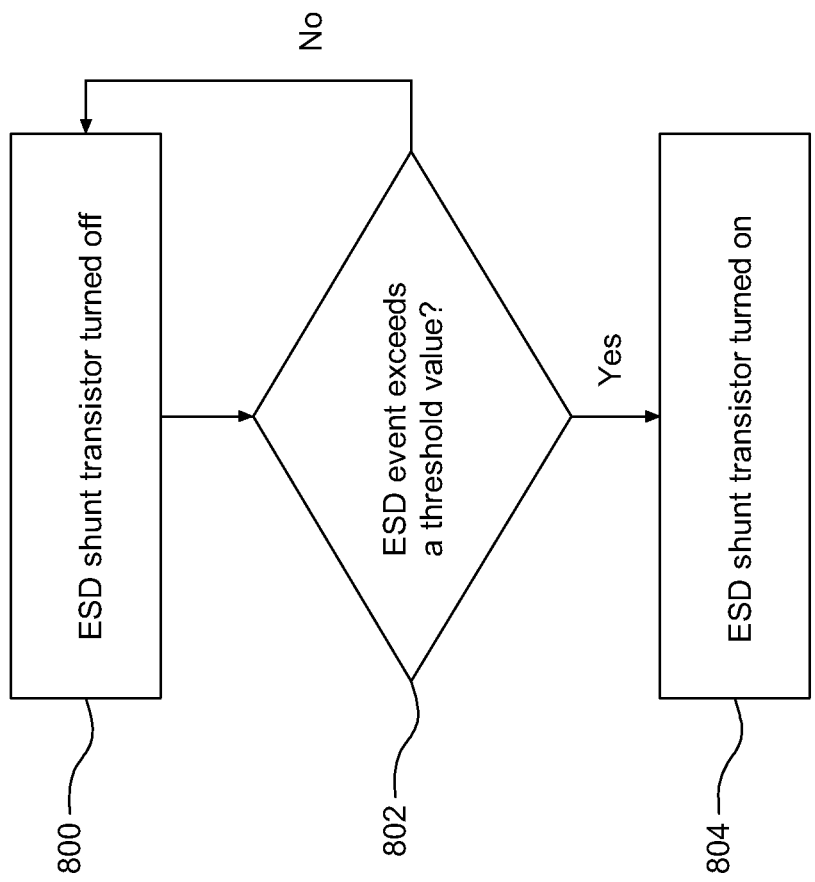
FIG. 8 is a diagram illustrating generally, by way of an example, but not by way of limitation, a method for shunting ESD in an IMD.

FIG. 8 is a diagram illustrating generally, by way of example, but not by way of limitation, a method for shunting ESD of an integrated circuit in an IMD. At 800, the ESD shunt transistor 206 can be in an inactive state. At 802, in case an ESD event exceeds a specified ESD event threshold value, the ESD clamp circuit detects an ESD event. The resistance value of the resistor 408, together with the capacitance value of the second capacitor 208, can determine the time constant for an ESD event. The time constant (T) can be the measure of the length in time for the discharge current to die down to a negligible value. The integrated circuit in the IMD can have the time constant of approximately 0.7 micro seconds (µs). The time constant (T) can be set by the aggregate capacitance (C) and the resistance (R), where T=RC.

The ESD event with voltage or energy exceeding a specified threshold value turns on the ESD shunt transistor 206. As discussed with respect to FIG. 2, a time for TDDB of the second capacitor dielectric material 226 of the second capacitor 208 in the ESD protection circuit 122 can be higher than that of the first capacitor dielectric material 214 of the first capacitor 204 located on the same integrated circuit 120. Hence, at 804, the ESD protection circuit 122 can turn on. The second capacitor 208 can be used in the ESD protection circuit 122 to shunt the ESD. As a result, a low-impedance path from the first supply rail 410 to the second supply rail 412 can be provided.

As discussed herein, the second capacitor dielectric material 226 of the second capacitor 208 can be configured to protect from a (TDDB) of the second capacitor dielectric material 226 of the second capacitor 208 in the ESD protection circuit 122. Hence, capacitor dielectric breakdown in the ESD protection circuit due to TDDB can be avoided by employing the second capacitor 208 in the ESD protection circuit 122. Hence, the second capacitor 208 can provide a more reliable IMD. The ESD protection circuits described herein can be included in an integrated circuit in an IMD, examples of which can include a pacemaker, a defibrillator, or a cardioverter, or other IMD incorporating the second capacitor.

Various Notes & Examples

Example 1 can include subject matter (such as an apparatus, a method, a means for performing acts, or a device readable medium including instructions that, when performed by the device, can cause the device to perform acts), such as can include or use an implantable medical device. The implantable medical device can include a housing. An integrated circuit can be carried within the housing. The integrated circuit can include a substrate. A first capacitor can be located directly or indirectly upon the substrate. The first capacitor can comprise an electrically conductive lower polysilicon terminal and an electrically conductive upper polysilicon terminal that is separated from the lower polysilicon terminal by a first capacitor dielectric material. The integrated circuit can include an electrostatic discharge (ESD) protection circuit. The ESD protection circuit can include an ESD shunt transistor. The ESD shunt transistor can be configured to be normally off, but can be configured to turn on and conduct between first and second power supply rails in response to an ESD event exceeding a specified ESD event threshold value. The integrated circuit can also include a second capacitor, located directly or indirectly upon the substrate. The second capacitor can be coupled to a control terminal of the ESD shunt transistor. The second capacitor can comprise a first substrate terminal and an electrically conductive second polysilicon terminal separated from the first substrate terminal by a second capacitor dielectric material. A capacitance value of the second capacitor can be specified to contribute to the specified ESD event threshold value.

Example 2 can include, or can optionally be combined with the subject matter of Example 1 to optionally include the integrated circuit comprising a bond pad. A first diode can be coupled between the bond pad and the first supply rail and configured to turn on to clamp a voltage of the bond pad to not exceed a voltage of the first supply rail by more than a turn-on voltage of the first diode. A second diode can be coupled between the bond pad and the second supply rail and configured to turn on to clamp a voltage of the bond pad to not fall below a voltage of the second supply rail by more than a turn-on voltage of the second diode. A thickness of the first capacitor dielectric material separating the lower and upper polysilicon terminals of the first capacitor can be greater than a thickness of the second capacitor dielectric material separating the first substrate terminal from the second polysilicon terminal.

Example 3 can include, or can optionally be combined with the subject matter of one or any combination of Examples 1 or 2 to optionally include, the second capacitor dielectric material comprising a native or grown oxide on a monocrystalline region of the substrate, and the first capacitor dielectric material comprising a material other than a native or grown oxide.

Example 4 can include, or can optionally be combined with the subject matter of one or any combination of Examples 1 through 3 to optionally include, the first capacitor dielectric material comprising a deposited oxide.

Example 5 can include, or can optionally be combined with the subject matter of one or any combination of Examples 1 through 4 to optionally include the first capacitor dielectric material comprising a spun-on oxide.

Example 6 can include, or can optionally be combined with the subject matter of one or any combination of Examples 1 through 5 to optionally include the first capacitor dielectric material comprising a sputtered oxide.

Example 7 can include, or can optionally be combined with the subject matter of one or any combination of Examples 1 through 6 to optionally include the second capacitor dielectric material comprising a native or dry grown oxide on a monocrystalline region of the substrate, and the first capacitor dielectric material comprising a wet-grown oxide.

Example 8 can include, or can optionally be combined with the subject matter of one or any combination of Examples 1 through 7 to optionally include the first capacitor dielectric material comprising a time-dependent dielectric breakdown time characteristic that is shorter than a time-dependent dielectric breakdown time characteristic of the second capacitor dielectric material.

Example 9 can include, or can optionally be combined with the subject matter of one or any combination of Examples 1 through 8 to optionally include the first capacitor dielectric material comprising a first leakage current value, and the second capacitor dielectric material comprising a second leakage current value that is less than the first leakage current value, and the first capacitor dielectric material comprising a first dielectric constant, and the second capacitor dielectric material comprises a second dielectric constant, and wherein the first dielectric constant exceeds the second dielectric constant.

Example 10 can include, or can optionally be combined with the subject matter of one or any combination of Examples 1 through 9 to optionally include the ESD shunt transistor comprising a field-effect transistor comprising a gate, a first source/drain, and a second source drain, and the second capacitor can be coupled between a first source/drain and the gate of the ESD shunt transistor.

Example 11 can include, or can optionally be combined with the subject matter of one or any combination of Examples 1 through 10 to optionally include a resistor that can be coupled between the gate of the ESD shunt transistor and the second source/drain of the ESD shunt transistor. A resistance value of the resistor, together with the capacitance value of the second capacitor, can be specified to contribute to the specified ESD event threshold value.

Example 12 can include, or can optionally be combined with the subject matter of one or any combination of Examples 1 through 11 to optionally include the first substrate region being located in a well region of the substrate.

Example 13 can include, or can optionally be combined with the subject matter of one or any combination of Examples 1 through 12 to optionally include the first substrate region being located in an epitaxial region of the substrate.

Example 14 can include, or can optionally be combined with the subject matter of one or any combination of Examples 1 through 13 to optionally include the second capacitor comprises a depletion-mode capacitor.

Example 15 can include, or can optionally be combined with the subject matter of one or any combination of Examples 1 through 13 to optionally include the second capacitor comprising an enhancement-mode capacitor.

Example 16 can include, or can optionally be combined with the subject matter of one or any combination of Examples 1 through 15 to optionally include, a buffer circuit coupled between the second capacitor and the control terminal of the ESD shunt transistor. The buffer circuit can be configured to drive the control terminal of the ESD shunt transistor.

Example 17 can include, or can optionally be combined with the subject matter of one or any combination of Examples 1 through 16 to optionally include the first and second supply rails being configured to be driven by a power supply circuit causing a voltage separation between the first and second supply rails of at least 10 Volts.

Example 18 can include, or can optionally be combined with the subject matter of one or any combination of Examples 1 through 17 to optionally include the second capacitor being formed from a field-effect transistor having a first source/drain region, a second source/drain region. The first source/drain region can be electrically shorted to the second source/drain region.

Example 19 can include, or can optionally be combined with the subject matter of one or any combination of Examples 1 through 18 to optionally include the field-effect transistor from which the second capacitor is formed comprising a transistor length that is substantially equivalent to a specified minimum transistor length of a fabrication process used to fabricate the first integrated circuit.

Example 20 can include, or can optionally be combined with the subject matter of one or any combination of Examples 1 through 19 to include subject matter (such as an apparatus, a method, a means for performing acts, or a device readable medium including instructions that, when performed by the device, can cause the device to perform acts), such as can include or use an implantable medical device. The implantable medical device can include a housing. An integrated circuit can be carried within the housing. The integrated circuit can include a substrate. A first capacitor can be located directly or indirectly upon the substrate. The first capacitor can comprise an electrically conductive lower polysilicon terminal and an electrically conductive upper polysilicon terminal that is separated from the lower polysilicon terminal by a first capacitor dielectric material, wherein the first capacitor dielectric material comprises a material other than a native or dry-grown oxide. An electrostatic discharge (ESD) protection circuit can include an ESD shunt transistor and a second capacitor. The ESD shunt transistor can be configured to be normally off, but configured to turn on and conduct between first and second power supply rails in response to an ESD event exceeding a specified ESD event threshold value. The ESD shunt transistor can comprise a field-effect transistor comprising a gate, a first source/drain, and a second source drain. The second capacitor can be coupled between a first source/drain and the gate of the ESD shunt transistor. The first and second supply rails can be configured to be driven by a power supply circuit causing a voltage separation between the first and second supply rails of at least 10 Volts. The second capacitor can be coupled to a control terminal of the ESD shunt transistor. The second capacitor can comprise a first substrate terminal and an electrically conductive second polysilicon terminal separated from the first substrate terminal by a second capacitor dielectric material. A capacitance value of the second capacitor can be specified to contribute to the specified ESD event threshold value. The second capacitor dielectric material can comprise a native or grown oxide on a monocrystalline region of the substrate. The second capacitor can be formed from a field-effect transistor having a first source/drain region, a second source/drain region, and wherein the first source/drain region is electrically shorted to the second source/drain region. A resistor can be coupled between the gate of the ESD shunt transistor and the second source/drain of the ESD shunt transistor. A resistance value of the resistor, together with the capacitance value of the second capacitor, can be specified to contribute to the specified ESD event threshold value. The integrated circuit can include a bond pad. A first diode can be coupled between the bond pad and the first supply rail and configured to turn on to clamp a voltage of the bond pad to not exceed a voltage of the first supply rail by more than a turn-on voltage of the first diode. A second diode can be coupled between the bond pad and the second supply rail and configured to turn on to clamp a voltage of the bond pad to not fall below a voltage of the second supply rail by more than a turn-on voltage of the second diode. A thickness of the first capacitor dielectric material separating the lower and upper polysilicon terminals of the first capacitor can be greater than a thickness of the second capacitor dielectric material separating the first substrate terminal from the second polysilicon terminal.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device, comprising:
a housing;
an integrated circuit carried within the housing, the integrated circuit including:
a substrate;
a first capacitor, located directly or indirectly upon the substrate, the first capacitor comprising an electrically conductive lower polysilicon terminal and an electrically conductive upper polysilicon terminal that is separated from the lower polysilicon terminal by a first capacitor dielectric material; and
an electrostatic discharge (ESD) protection circuit, comprising:
an ESD shunt transistor, configured to be normally off, but configured to turn on and conduct between first and second power supply rails in response to an ESD event exceeding a specified ESD event threshold value; and
a second capacitor, located directly or indirectly upon the substrate, the second capacitor coupled to a control terminal of the ESD shunt transistor, the second capacitor comprising a first substrate terminal and an electrically conductive second polysilicon terminal separated from the first substrate terminal by a second capacitor dielectric material, a capacitance value of the second capacitor specified to contribute to the specified ESD event threshold value.

2. The device of claim 1, wherein the integrated circuit comprises:
a bond pad;
a first diode, coupled between the bond pad and the first supply rail and configured to turn on to clamp a voltage of the bond pad to not exceed a voltage of the first supply rail by more than a turn-on voltage of the first diode; and
a second diode, coupled between the bond pad and the second supply rail and configured to turn on to clamp a voltage of the bond pad to not fall below a voltage of the second supply rail by more than a turn-on voltage of the second diode; and
wherein a thickness of the first capacitor dielectric material separating the lower and upper polysilicon terminals of the first capacitor is greater than a thickness of the second capacitor dielectric material separating the first substrate terminal from the second polysilicon terminal.

3. The device of claim 1, wherein the second capacitor dielectric material comprises a native or grown oxide on a monocrystalline region of the substrate, and wherein the first capacitor dielectric material comprises a material other than a native or grown oxide.

4. The device of claim 3, wherein the first capacitor dielectric material comprises a deposited oxide.

5. The device of claim 3, wherein the first capacitor dielectric material comprises a spun-on oxide.

6. The device of claim 3, wherein the first capacitor dielectric material comprises a sputtered oxide.

7. The device of claim 1, wherein the second capacitor dielectric material comprises a native or dry grown oxide on a monocrystalline region of the substrate, and wherein the first capacitor dielectric material comprises a wet-grown oxide.

8. The device of claim 1, wherein the first capacitor dielectric material comprises a time-dependent dielectric breakdown time characteristic that is shorter than a time-dependent dielectric breakdown time characteristic of the second capacitor dielectric material.

9. The device of claim 1, wherein:
the first capacitor dielectric material comprises a first leakage current value, wherein the second capacitor dielectric material comprises a second leakage current value, and wherein the second leakage current value is less than the first leakage current value; and
the first capacitor dielectric material comprises a first dielectric constant, wherein the second capacitor dielectric material comprises a second dielectric constant, and wherein the first dielectric constant exceeds the second dielectric constant.

10. The device of claim 1, wherein the ESD shunt transistor comprises a field-effect transistor comprising a gate, a first source/drain, and a second source drain, and wherein the second capacitor is coupled between a first source/drain and the gate of the ESD shunt transistor.

11. The device of claim 10, comprising a resistor coupled between the gate of the ESD shunt transistor and the second source/drain of the ESD shunt transistor, and wherein a resistance value of the resistor, together with the capacitance value of the second capacitor, are specified to contribute to the specified ESD event threshold value.

12. The device of claim 1, wherein the first substrate region is located in a well region of the substrate.

13. The device of claim 1, wherein the first substrate region is located in an epitaxial region of the substrate.

14. The device of claim 1, wherein the second capacitor comprises a depletion-mode capacitor.

15. The device of claim 1, wherein the second capacitor comprises an enhancement-mode capacitor.

16. The device of claim 1, comprising a buffer circuit coupled between the second capacitor and the control terminal of the ESD shunt transistor, the buffer circuit configured to drive the control terminal of the ESD shunt transistor.

17. The device of claim 1, wherein the first and second supply rails are configured to be driven by a power supply circuit causing a voltage separation between the first and second supply rails of at least 10 Volts.

18. The device of claim 1, wherein the second capacitor is formed from a field-effect transistor having a first source/drain region, a second source/drain region, and wherein the first source/drain region is electrically shorted to the second source/drain region.

19. The device of claim 18, wherein the field-effect transistor from which the second capacitor is formed comprises a transistor length that is substantially equivalent to a specified minimum transistor length of a fabrication process used to fabricate the first integrated circuit.

20. An implantable medical device, comprising:
a housing;
an integrated circuit carried within the housing, the integrated circuit including:
a substrate;
a first capacitor, located directly or indirectly upon the substrate, the first capacitor comprising an electrically conductive lower polysilicon terminal and an electrically conductive upper polysilicon terminal that is separated from the lower polysilicon terminal by a first capacitor dielectric material, wherein the first capacitor dielectric material comprises a material other than a native or dry-grown oxide;
an electrostatic discharge (ESD) protection circuit, comprising:
an ESD shunt transistor, configured to be normally off, but configured to turn on and conduct between first and second power supply rails in response to an ESD event exceeding a specified ESD event threshold value, wherein the ESD shunt transistor comprises a field-effect transistor comprising a gate, a first source/drain, and a second source drain, and wherein the second capacitor is coupled between a first source/drain and the gate of the ESD shunt transistor, and wherein the first and second supply rails are configured to be driven by a power supply circuit causing a voltage separation between the first and second supply rails of at least 10 Volts;
a second capacitor, coupled to a control terminal of the ESD shunt transistor, the second capacitor comprising a first substrate terminal and an electrically conductive second polysilicon terminal separated from the first substrate terminal by a second capacitor dielectric material, a capacitance value of the second capacitor specified to contribute to the specified ESD event threshold value, wherein the second capacitor dielectric material comprises a native or grown oxide on a monocrystalline region of the substrate, wherein the second capacitor is formed from a field-effect transistor having a first source/drain region, a second source/drain region, and wherein the first source/drain region is electrically shorted to the second source/drain region; and
a resistor coupled between the gate of the ESD shunt transistor and
the second source/drain of the ESD shunt transistor, and wherein a resistance value of the resistor, together with the capacitance value of the second capacitor, are specified to contribute to the specified ESD event threshold value;
a bond pad;
a first diode, coupled between the bond pad and the first supply rail and configured to turn on to clamp a voltage of the bond pad to not exceed a voltage of the first supply rail by more than a turn-on voltage of the first diode; and
a second diode, coupled between the bond pad and the second supply rail and configured to turn on to clamp a voltage of the bond pad to not fall below a voltage of the second supply rail by more than a turn-on voltage of the second diode; and
wherein a thickness of the first capacitor dielectric material separating the lower and upper polysilicon terminals of the first capacitor is greater than a thickness of the second capacitor dielectric material separating the first substrate terminal from the second polysilicon terminal.

* * * * *